United States Patent [19]

Anderson et al.

[11] 4,254,142

[45] Mar. 3, 1981

[54] DITHIOCARBANILIC ACIDS AND USE THEREOF AS IMMUNOSUPPRESSIVE AGENT

[75] Inventors: David J. Anderson, Kalamazoo; Barbara E. Loughman, Richland, both of Mich.

[73] Assignee: The Upjohn Company, Kalamazoo, Mich.

[21] Appl. No.: 64,784

[22] Filed: Aug. 8, 1979

[51] Int. Cl.$^3$ ..................... A61K 31/27; C07C 155/08
[52] U.S. Cl. ................................ 424/300; 260/455 A
[58] Field of Search .................... 260/455 A; 424/300

[56] References Cited

U.S. PATENT DOCUMENTS 3,075,875  1/1963  Margot ,............................ 260/455 A

*Primary Examiner*—Henry R. Jiles
*Assistant Examiner*—Robert C. Whittenbaugh
*Attorney, Agent, or Firm*—Sidney B. Williams, Jr.

[57] ABSTRACT

Norbornyl thio- and dithiocarbanilic acid are described. The compounds possess immunoregulatory activity. Also provided are compositions containing and methods of using them.

18 Claims, No Drawings

DITHIOCARBANILIC ACIDS AND USE THEREOF AS IMMUNOSUPPRESSIVE AGENT

BACKGROUND OF THE INVENTION

1. Field of the Invention

This invention concerns novel norbornyl derivatives of thio- and dithio-carbanilic acid and their use as immunoregulatory agents.

Some of the compounds also have shown activity as hypotensive agents.

2. The Prior Art

Certain derivatives of thio and dithiocarbanilic acids are known in the prior art.

See, for example, Garraway, J. L., J. Chem. Soc. 1961: 3733 which describes the ω-carboxyalkyl dithiocarbanilates as precursors for the corresponding cyclic lactams (i.e., rhodanines an thiazine analogs). Further with respect to the production of rhodanine or thiazine analogs for corresponding ω-carboxyalkyl dithiocarbanilate precursors, see U.S. Pat. No. 3,781,434; Brown, F. C., et al., J.A.C.S., 78: 384 (1956); and Werbel, L. M., et al., J. Med. Chem. 11(2):364 (1968). The former reference describes the antiarthritic use of the cyclic thiazines, while the latter references describe the cyclic rhodanine derivations as antifungicidal, antibacterial, and antimalarial agents.

ω-Carboxymethyl 2,3-dihalo-dithiocarbanilates are described in British Published Secification No. 1,153,487 as anthelmintics. Further, U.S. Pat. No. 3,089,877 describes ω-(amidocarbonyl)alkyl dithiocarbonylates as fungicidal agents. Finally, U.S. Pat. No. 3,686,413 describes the anthelmintic use of dithiocarbanilates, including, inter alia, compounds of the formula

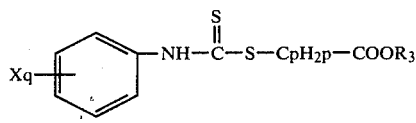

wherein $R_3$ is hydrogen or alkyl of 1 to 4 carbon atoms, inclusive;

wherein p is the integer 1 or 2;

wherein X is chloro, bromo, or nitro; and wherein q is the integer 0 to 5, inclusive.

Thiocarbanilates, dithiocarbanilates, bisthiocarbanilates and bisdithiocarbanilates are disclosed as plant treating agents in British Pat. No. 811,861. These compounds have the formula

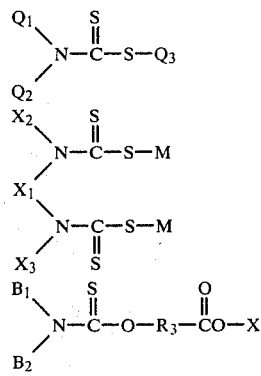

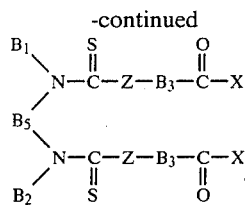

wherein $Q_1$, $Q_2$ and $Q_3$ may be hydrogen, alkyl or aralkyl groups, $X_1$ designates a bivalent hydrocarbon group or a bivalent aliphatic chain containing more than 3 carbon atoms and divided by at least one nitrogen atom into alkylene groups consisting each of at least two carbon atoms, $X_2$ and $X_3$ designate hydrogen, or bivalent hydrocarbon atoms, i.e., when $X_2$ and $X_3$ form a heterocyclic ring with the bond N—X—N. M designates a salt forming group or a metal atom. $B_1$ and $B_2$ designate hydrogen atoms and/or alkyl-groups or constitute with the nitrogen atoms, a ring of 6 atoms at the most, $B_3$ designates a bivalent, if desired substituted, alkylene, aralkylene or arylene group. $B_5$ designates a bivalent alkylene, aralkylene or arylene group, for example, a phenylene group, or together with two nitrogen atoms and the two groups $R_2$ forms a ring of not more than 6 atoms, or together with one nitrogen atom and the group $R_2$ attached to this atom, a ring of not more than 6 atoms, X designates an $NH_2$, a substituted $NH_2$—group, an OH—group in which the hydrogen atom is replaced by a cation, an alkyl, aralkyl- or arylgroup and finally Z designates an oxygen atom or a sulphur atom.

In addition to the uses of the dithiocarbanilates described above, certain chemical and biological investigations relating to such compounds have been undertaken and are reported in papers deposited in The California Polytechnic State University Library in San Luis Obispo, California. These papers are identified by author and title, as follows: Bello, J., "Some Effects of Newly Synthesized Thiocarbamates on Blood and Organ Parameters in the Mouse and Pig", Booth, J. "The Effects of 3-(N-Meta Fluorophenyl Dithiocarbamoyl) Propanic Acid on BAPN Induced Lathyrism in the Rat"; Burdick, P. R., "Warfarin Activity Modification and Other Effects of Some New Thiocarbamates in Mice"; Foster, R., "Modification of the Erythrocyte Membrane in Swine"; Jones, P., "Histological Effects of Carbamate Derivatives on the Spleen and Thymus of Swiss-Webster Mice"; Lash, L. D., "Leukocyte Depression and Other Responses in the Mouse, Produced by Datisca and a Novel Thiocarbamate"; Meyer, O., "The Effects of 3(N-Metafluorophenyl)Dithiocarbamoyl Propanoic Acid on the Lathrytic Condition Induced by Beta-Aminopropionitrile", Mortensen, M. L., "The Synthesis of Some of the Reaction Products of Isocyanates and Isothiocyanates with 3-Mercaptopropionic Acid"; and Reid, A., "Modification of Lathyrism in Rats by Three New Thiocarbamates".

Belgian Pat. No. 862,725 (Derwent Accession No. 33497/19) discloses penicillamine compounds and their acid addition salts that have immunosuppressive and antiinflammatory activity. The compounds have the formula

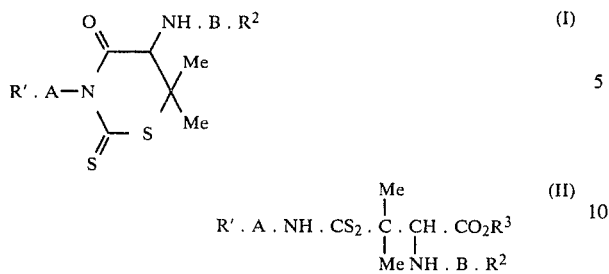 (I)

 (II)

(where R' is H, alkyl, alkenyl, alkoxycarbonyl, aryl, diphenylmethyl, heteroaryl, or the group $$-N\begin{matrix}R^4\\R^5\end{matrix};$$

$R^4$ and $R^5$ singly are alkyl aryl or aralkyl, or $R^4$ and $R^5$ together with the attached N or O atom, $R^2$ is alkyl, aryl, aralkenyl, aryloxyalkyl, or heteroaryl, optionally subtituted by alkyl, $R^3$ is H or alkyl, A is 1–5C alkylene, B is alkyl, $R^3$ is H or alkyl, A is 1–5C alkylene, B is —CO— or —CO$_2$—). In each case, the aryl, aralkyl, aralkenyl or heteroaryl groups are optionally substituted by $\leq 1$ alkyl, alkoxy, halo, NO$_2$, CF$_3$, methylenedioxy, alkylsulphonamido, arylsulphonamido, trifluoromethylsulphonamido, acyl or acetoxy groups.

Immunoregulatory agents may be either immunosuppressive or immunostimulatory. For the purposes of the present invention immunoregulation shall make reference to the process of immunosuppression in response to a disease or other condition results from hyperimmunity in the animal or patient. Immunosuppressive use of ω-carboxyalkyl, the use of immunosuppressive agents in the treatment of and ω-(alkoxycarbonyl)alkyl esters of dithiocarbanilic acid and certain aryl-substituted acids related thereto are found in U.S. Pat. No. 4,110,440 and copending Ser. No. 848,433. For a comprehensive review of the use of immunosuppressive agents in the hyperimmunity diseases, see Camiener, G. W. et al., Progress in Drug Research 16:67 (1972) and Wechter, W. J., et al., Progress in Drug Research 20:573 (1976).

Many known immunosuppressive agents are cytotoxic and are believed in part to accomplish the immunosuppressive effects via a cytotoxic mechanism on the immunoactive organs (e.g., bone marrow and thymus). For example, the known antineoplastic agents, cyclohosphamide has been used in the treatment of arthritis. See Skinner, M. D., et al., Rheumatology 5:1 (1974).

Finally, anthelmintics such as niridazole have been employed immunosuppressively to control allograft rejection; while an other anthelmintic, levamisole, is apparently a non-specific stimulator of the immune system. See Daniels, J. D. et al., J. Immuno, 115–1414 (1975) and Renorex, G., et al., J. Immun. 109:761 (1972).

SUMMARY OF THE INVENTION

This invention pertains to compounds having the formula

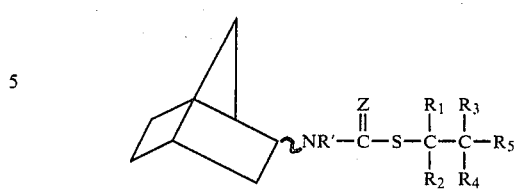

wherein $R_1$ through $R_4$ are the same or different and are selected from the group consisting of hydrogen, alkyl of from 1 to 8 carbon atoms, inclusive; and aralkyl of from 7 to 20 carbon atoms, inclusive; R' is selected from the group consisting of hydrogen and alkyl of from 1 to 8 carbon atoms, inclusive; and Z is selected from the group consisting of oxygen and sulfur; $R_5$ is —(CH$_2$)$_{nA}$ wherein A is selected from the group consisting of carboxyl, carboxylic lower alkylester, carboxylic amide group having the formula

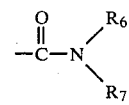

wherein $R_6$ and $R^7$ are the same or different and are selected from the group consisting of hydrogen and lower alkyl of from 1 to 8 carbon atoms, inclusive: cyano and an amine group having the formula

wherein R'' and R''' are the same or different and are selected from the group consisting of hydrogen and alkyl of from 1 to 8 carbon atoms, inclusive; n is an integer of from 0 to 3; with the proviso that when $R_5$ is cyano or a carboxylic amide group, $R_3$ or $R_4$ must always be hydrogen; and pharmaceutically acceptable salts of compounds wherein $R_5$ is an amine or carboxyl group. The invention also includes the immunosuppressive use of the above described compounds.

"Lower alkyl" means alkyl of from 1 to 8 carbon atoms, inclusive. For example, methyl, ethyl, propyl, butyl, pentyl, hexyl, heptyl and octyl and isomeric forms thereof.

The novel thio and dithiocarbanolic acid derivatives of this invention are prepared by methods analogous to those known in the art. For example, see the methods referred to in U.S. Pat. Nos. 3,686,413 and 3,781,434 and British Pat. No. 811,861 described above. Accordingly, the compounds of the present invention are prepared by reacting the appropriate arylisothiocyanate with the appropriate ω-(carboxycarbonyl)alkylthiol. The reaction proceeds at ambient temperature, being slightly exothermic, and is ordinarily complete within about one hour. Preferred reaction solvents are pyridine, benzene or aqueous trimethylamine. Recovery of the novel reaction product proceeds by conventional means, e.g., evaporation of solvent. The required starting materials for the present transformations are readily available or can be synthesized by readily available means.

Compounds wherein $R_5$ is other than carboxyl can also be prepared by methods well known in the art. For example, compounds wherein $R_5$ is carboxylic alkylester can be prepared from the corresponding carboxylic acids by methods well known in the art for esterifying carboxylic acids.

Compounds wherein $R_5$ is cyano can be prepared in accordance with the following schematic flow chart.

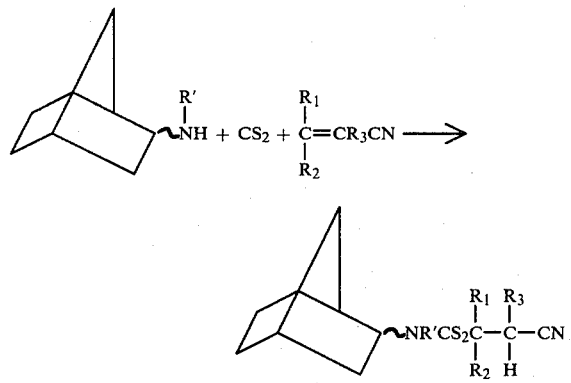

wherein $R'$, $R_1$, $R_2$ and $R_3$ are the same as defined above.

The reaction can be conducted in the presence or absence of a solvent at a temperature of between 25° and 55° for a period of between 5 and 60 minutes. Solvents that can be used include pyridine, water or ethanol. The preferred solvent is ethanol.

Compounds wherein $R_5$ is carboxylic amide can be prepared in accordance with the following schematic diagram.

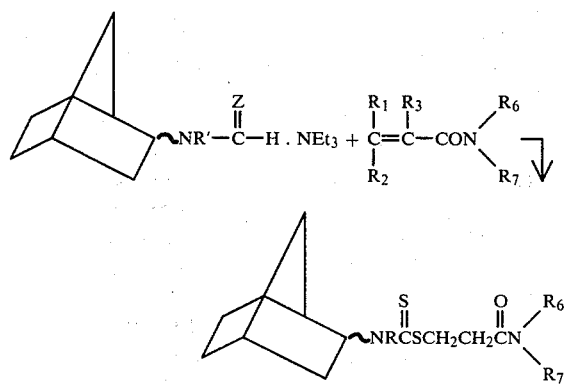

wherein $R'$, $R_1$, $R_2$, $R_3$, $R_6$, $R_7$, Y and Z are the same as defined above.

This reaction can be conducted in the presence or absence of a solvent at a temperature of between 25° and 55° for a period of between 1 hour and 24 hours. Solvents that can be used include pyridine, water and ethanol. The preferred solvent is ethanol.

Compounds wherein $R_5$ is an amino group can be prepared as follows:

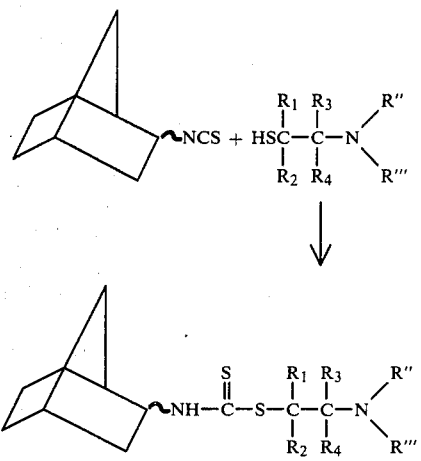

This reaction may be conducted in the absence or presence of a solvent at a temperature of between 25° and 55° for a period of about 1 to 2 hours. Solvents that can be used include ethanol, pyridine, benzene and aqueous trimethylamine. The preferred solvent is aqueous.

With respect to the novel method described above for producting immunosuppression in mammals exhibiting hyperimmunity disease, the use of this method in man is especially intended. However, the use in other mammals, such as canine, feline, bovine, and equine species is further intended.

Hyperimmunity diseases encompassed by the present method include transplant rejection phenomena and autoimmune diseases.

With respect to the transplant rejection phenomena, the present invention relates to allograph rejection phenomena in organ transplanation, including graft-versus-host disease in allographic bone marrow transplantation.

With regard to the autoimmune disease encompassed by the present method, there is included rheumatoid arthritis, psoriatic arthritis, systemic lupus erythematosus, regional enteritis, chronic active hepatitis, nephrotic syndrome, glomerulonephritis, lupus nephritis, and ulcerative colitis.

In the use of the present invention in transplant rejection phenomena, advantageous results ranging from prolongation of the viability of the transplanted tissue to complete cessation of the rejection process are obtained. In the treatment of autoimmune diseases by the present method, advantageous results ranging from significant symptomatic relief to cessation of the underlying inflammatory process are obtained.

In the treatment of the hyperimmunity diseases described above, the requisite clinical endpoint is the suppression of the mammal's immune response, thereby effecting amelioration or cure of the hyperimmunity disease. Accordingly, the present invention contemplates use of effective dosages of the dithiocarbanilate such that the disease progress is first halted and thereafter reversed. The amount of dithiocarbanilate required depends upon a wide variety of factors including the particular compound selected, the age, weight and condition of the mammal being treated, the severity of the particular hyperimmune disease being treated, and the response of the mammal to treatment.

In order to obtain the efficacious results provided by the present invention, any systemic route of administration is acceptable. However, for convenience, the preferred route of administration is oral, although other systemic routes of administration provide equivalent activity at the appropriate dose. Thus, intravenous injection or infusion, subcutaneous injection, or administration in the form of rectal or vaginal suppository represent alternate routes of administration. Regardless of the route of administration selected, the dithiocarbanilate is formulated in a pharamceutically acceptable dosage form by conventional methods available in the pharamceutical arts.

Accordingly, when compressed tablets are desired for oral administration, the dithiocarbanilate is combined with the desired inert ingredients and thereafter compressed by conventional means into a tablet containing the desired quantity of the dithiocarbanilate. In the case of parenteral administration, sterile solutions for injection or infusion are prepared in accordance with readily available techniques.

After the onset of the hyperimmunity disease has been diagnosed by the attending physician or veterinarian, the treatment with the dithiocarbanilate in accordance with the present method may be initiated promptly. In cases where the dithiocarbanilate is the sole immunosuppressive agent to be employed in the treatment of the hyperimmunity disease, an initial dosage between 5 and 50 mg/kg/day is employed. When initial dosages at the lower end of the above range are employed, the mammal's progress is monitored and dosages on subsequent days are increased in the event that the patient or animal response is deemed by the attending physician or veterinarian to be absent or insufficient. When dosage as high as about 100 mg/kg/day are selected, the systemic toxicity of the dithiocarbanilate must be carefully evaluated and subsequent dosages determined by evaluating the benefits of the drug in relationship to any such toxic manifestations.

For convenience, dosages may be administered once daily or, more preferably, administered at periodic intervals throughout the day. Accordingly, in man the dithiocarbanilate is advantageously administered at 4 or 8 hour intervals throughout the day.

Accordingly, the present method provides a new and unexpected use for a class of dithiocarbanilates previously known to be useful for unrelated purposes. Additionally, the present invention provides new and structurally distinct thio- and dithiocarbanilates which in accordance with the present invention surprisingly and unexpectedly exhibit immunosuppressive properties rendering them useful in the treatment of hyperimmunity diseases.

Finally, the unique chemical structure of these thio- and dithiocarbanilates provides these compounds with advantageous absorption characteristics, resulting in more prolonged immunosuppressive activity with fewer undesired systemic effects.

The following described preparation of new compounds according to this invention are indicative of the scope of the invention and are not to be construed as limitative. These examples indicate the best mode presently known to the inventor.

EXAMPLE 1

Exo-(±)-3-[[bicyclo[2,2,]hept-2-ylamino)-thioxomethyl]thio]propanoic acid

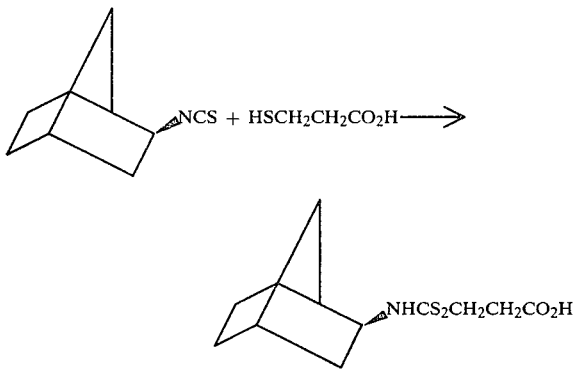

(±)-Exo-2-norbornylisothiocyanate (7.65 g, 50 mmol) and β-mercapto propionic acid (5.30 g, 50 mmol) are stirred for 30 minutes in 25 percent aqueous trimethylamine (30 ml.) After cooling in ice, concentrated hydrochloric acid is added to precipitate a gummy solid which is dissolved in ether (600 ml) and washed with water (250 ml). After drying over magnesium sulfate there is obtained an oil (14.2 g). Chromatography over silica gel, eluting with chloroform-acetic acid (99:1) afforded pure Exo-(±)-3-[[bicyclo[2,2,]hept-2-ylamino)thioxomethyl]thio]propanoic acid as white crytals (11.1 g) from chloroform-hexane: m.p. 116°–118°.

Analysis Calc'd for $C_{11}H_{17}NO_2S_2$: C, 50.9; H, 6.6; N, 5.4; S, 24.7; Found: C, 51.0; H, 6.6; N, 5.7; S, 23.9.

IR: λmax (Nujol) 3220 (NH), 1730 (CO), 1710 (CO) cm−1

Following the procedure of Example 1, but substituting the appropriately substituted mercapato-carboxylic acid for β-mercapto proionic acid there is obtained Exo-(±)-3-[[(bicyclo[2,2,1]hept-2-ylamino)thioxomethyl]thio]-2-methylpropanoic acid.

Exo-(±)-3-[[(bicyclo[2,2,1]hept-2-ylamino)thioxomethyl]thio]-3,3-dimethylpropanoic acid.

Exo-(±)-3-[[(bicyclo]2,2,1]hept-2-ylamino)thioxomethyl]thio]-2,3-dimethylbutanoic acid.

The above acids can be converted to their corresponding lower alkyl ester by procedures well known in the art for esterifying carboxylic acids.

EXAMPLE 2

Endo-(+)-3-[[(bicyclo[2,2,1]-hept-2-ylamino)thiomethyl]thio]propanoic acid

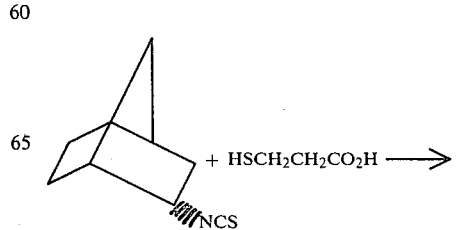

-continued

[Structure: norbornyl with NHCS₂CH₂CH₂CO₂H (endo)]

(±)-Endo-2-norbornylisothiocyanate (7.65 g, 50 mmol) and β-mercaptopropionic acid (5.50 g, 52 mmol) are stirred in 30 ml of 25 percent aqueous trimethylamine for 30 minutes. After cooling in ice, concentrated hydrochloric acid is added to yield a brown gummy solid. The solid is dissolved in ether (400 ml) and washed with water (200 ml). After drying over magnesium sulfate a reddish oil (12.6 g) is obtained which soon solidifies. Several recrystallizations from chloroform-hexane gives endo-(+)-3-[[(bicyclo[2,2,1]hept-2-ylamino)thioxomethyl]thio]propanoic acid as a white solid, m.p. 138°–141°.

Analysis Calc'd for $C_{11}H_{17}NO_2S_2$: C, 50.9; H, 6.6; N, 5.4; S, 24. Found: C, 50.5; H, 6.7; N, 5.5; S, 24.0.

IR: λmax (Nujol) 3225 (NH), 1730 (CO) cm−1.

Following the procedure of Example 2, but substituting the appropriately substituted mercaptocarboxylic acid for β-mercaptopropionic acid there is obtained (±)-Endo-3-[[(bicyclo[2,2,1]hept-2-ylamino)thioxomethyl]thio]-2-methylpropanoic acid.

(±)-Endo-3-[[(bicyclo[2,2,1]hept-2-ylamino)thioxomethyl]thio]-3,3-dimethylpropanoic acid.

(±)-Endo-3-[[(bicyclo[2,2,1]hept-2-ylamino)thioxomethyl]thio]-2,3-dimethylbutanoic acid.

The corresponding lower alkyl ester of the above acids can be prepared by conventional techniques known in the art for esterifying carboxylic acids.

$$R_5 = \text{Amide } \overset{O}{\overset{\|}{C}}-NRR$$
$$= CN$$
$$= N\diagup^R_{\diagdown R}$$

R′ = Other than hydrogen

EXAMPLE 3

Exo-(+)-3-[[N-methyl-(bicyclo[2,2,1]hept-2-ylamino)-thioxomethyl]thio]propanoic acid

[Structure: norbornyl with CH₃-NH + CS₂ + CH₂=CHCO₂H →]

[Structure: norbornyl with N(CH₃)CS₂CH₂CH₂CO₂H]

The exo-N-methylnorbornyl-2-amino (0.1 mole), triethylamino (0.1 mole) and carbon disulfide (0.1 mole) are warmed gently for about 10 minutes, then allowed to cool. Acrylic acid (0.1 mole) dissolved in ethanol (50 ml) [or water (50 mole)] is added and the mixture stirred for 1 to 24 hours. After which time the product is either filtered directly or precipitated with 10% HCl. Recrystallization is from acetone-hexane. [3-bromopropionic acid (0.1 mole) dissolved in 100 ml g 1 N NaOH may be substiuted for the acrylic acid with similar results].

In this manner the following are obtained:

Exo-(±)-3-[[N-propyl-(bicyclo[2,2,1]hept-2-ylamino)thioxomethyl]thio]-propanoic acid.

Exo-(±)-3-[[N-ethyl-(bicyclo[2,2,1]hept-2-ylamino)-thioxomehyl]thio]-propanoic acid.

Substituting either acrylonitrile or acylamide for acrylic acid in the previous example the following were obtained:

Exo-(±)-3-[[N-methyl-(bicyclo[2,2,1]hept-2-ylamino)-thioxomethyl]thio]propionitrile.

Exo-(±)-3-[[N-ethyl-(bicyclo[2,2,1]hept-2-ylamino)-thioxomethyl]thio]propionitrile.

Exo-(±)-3-[[N-methyl-(bicyclo[2,2,1]hept-2-ylamino)-thioxomethyl]thio]propionamide.

Exo-(±)-3-[[N-ethyl-(bicyclo[2,2,1]hept-2-ylamino)-thioxomethyl]thio]propionamide.

Exo-(±)-3[[NZpropyl-(bicyclo[2,2,1]hept-2-ylamino)-thioxomethyl]thio]propionamide.

EXAMPLE 4

Endo-(±)-[[N-methyl-(bicyclo[2,2,1]hept-2-ylamino)-thioxomethyl]thio]propanoic acid

[Structure: norbornyl with CH₃-NH + CS₂ + CH₂=CHCO₂H →]

[Structure: norbornyl with N(CH₃)CS₂CH₂CH₂CO₂H]

The endo-N-methylnorbornyl-2-amine (0.1 mole), triethylamino (0.1 mole) and carbon disulfate (0.1 mole) are warmed gently for about 10 minutes, then allowed to cool. Acrylic acid (0.1 mole) dissolved in ethanol (50 ml) [or water (50 ml)] is added and the mixture stirred for 1 to 24 hours. After which time the product is either filtered directly or precipitated with 10 percent HCL. Recrystallization is from acetone-hexane. [3-Bromopropionic acid] (0.1 mole) dissolved in 100 ml of 1 N NaOH may be substituted for the acrylic acid with similar results.

In this manner the following are obtained:

Endo-(±)-3-[[N-propyl-(bicyclo[2,2,1]hept-2-ylamino)-thioxomethyl]thio]propanoic acid, Endo-(±)-3-[N-ethyl-(bicyclo[2,2,1]hept-2-ylamino)-thioxomethyl]thio]propanoic acid, Substituted either acrylonitrile or acrylamide for acrylic acid in the previous example, the following were obtained:

Endo-(±)-[[N-methyl-(bicyclo[2,2,1]hept-2-ylamino)-thioxomethyl]thio]propanitrile, Endo-(±)-3-[[N-methyl-(bicyclo[2,2,1]hept-2-ylamino)-thioxomethyl]thio]propanitrile, Endo-(±)-3[[N-propyl-(bicyclo[2,2,1]hept-2-ylamino)-thioxomehyl]thio]propionitrile, Endo-(±)-3-[[N-methyl-(bicyclo[2,2,1]hept-2-ylamino)thioxomethyl]thio]propionamide, Endo-(±)-[[N-ethyl-(bicyclo[2,2,1]hept-2-ylamino)-thioxomethyl]thio]propionamide, Endo-(±)-3[[N-propyl-(bicyclo[2,2,1]hept-2-ylamino)-thioxomethyl]thio]propionamide.

Example 5 N,N-dimethyl-N-[[[exo-2-(bicyclo[2,2,1]hept-2-ylamino)thioxomethyl]thio]ethyl]amine

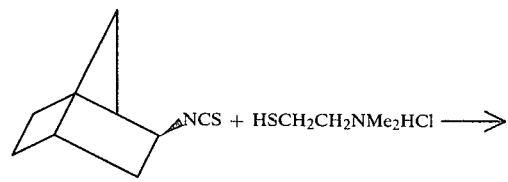

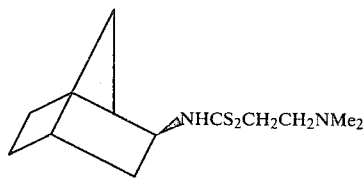

The isothiocyanate (0.1 mole) is added to a solution of dimethylamino ethanethiol hydrochloride (0.1 mole) and triethylamine (0.2 mole) in ethanol (100 ml). Stirring is continued for 3 to 4 hours after which time the product is filtered and recrystallized from methanol-water.

EXAMPLE 6

N,N-dimethyl-N-[[[endo-2-(bicyclo[2,2,1]hept-2-ylamino)thioxomethyl]thio]ethyl]amine

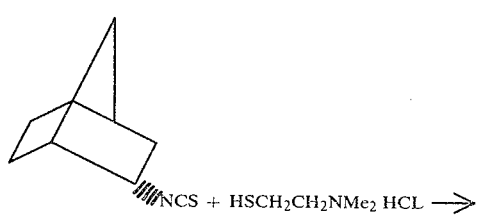

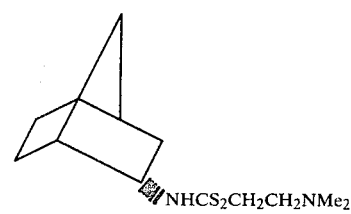

The isothiocyanate (0.1 mole) is added to a solution of dimethylamino ethanethio hydrochloride (0.1 mole) and triethylamine (0.2 mole) in ethanol (100 ml). Stirring is continued for 3 to 4 hours after which time the product is filtered and recrystallized from methanol-water.

We claim:

1. A compound having the formula

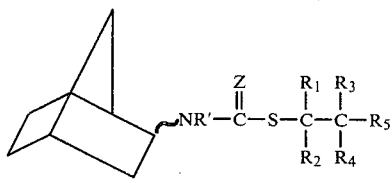

wherein $R_1$ through $R_4$ are the same or different and are selected from the group consisting of hydrogen and alkyl of from 1 to 3 carbon atoms, inclusive; $R'$ is selected from the group consisting of hydrogen and alkyl of from 1 to 8 carbon atoms, inclusive; Z is selected from the group consisting of oxygen and sulfur; $R_5$ is $-(CH_2)_nA$ wherein A is selected from the group consisting of carboxyl, carboxylic lower alkylester, carboxylic amide group having the formula

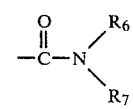

wherein $R_6$ and $R_7$ are the same or different and are selected from the group consisting of hydrogen and lower alkyl of from 1 to 8 carbon atoms, inclusive; cyano and an amine group having the formula

wherein $R''$ and $R'''$ are the same are different and are selected from the group consisting of hydrogen and alkyl of from 1 to 8 carbon atoms, inclusive; with the proviso that when $R_5$ is a cyano or a carboxylic amide group; $R_3$ or $R_4$ must always be hydrogen; and pharmaceutically acceptable salts of compounds wherein $R_5$ is an amine or carboxyl group.

2. A compound according to claim 1 having the formula

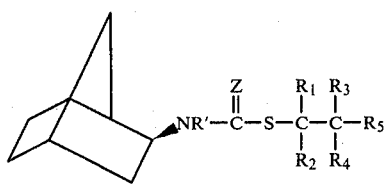

wherein $R_1$ thru $R_5$, $R'$, and $Z$ are the same as in claim 1.

3. A compound according to claim 2 wherein $R_5$ is carboxyl and $Z$ is sulfur.

4. A compound according to claim 3, Exo-($\pm$)-3-[[(bicyclo[2,2,1]hept-2-ylamino)thioxomethyl]thio]-propanoic acid.

5. A compound according to claim 1, having the formula

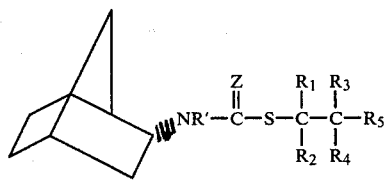

wherein $R_1$ thru $R_5$, $R'$, and $Z$ are the same as in claim 1.

6. A compound according to claim 5 wherein $R_5$ is carboxyl, and $Z$ is sulfur.

7. A compound according to claim 6, Endo-($\pm$)-3-[[(bicyclo)[2,2,1]hept-2-ylamino)thioxomethyl]thio]-propanoic acid.

8. A composition useful as an immunoregulatory agent comprising an effective amount of a compound having the formula

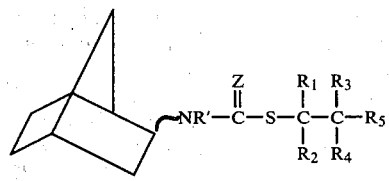

wherein $R_1$ through $R_4$ are the same or different and are selected from the group consisting of hydrogen, alkyl of from 1 to 8 carbon atoms, inclusive; and aralkyl of from 7 to 20 carbon atoms, inclusive; $R'$ is selected from the group consisting of hydrogen and alkyl of from 1 to 8 carbon atoms, inclusive; $Z$ is selected from the group consisting of oxygen and sulfur; $R_5$ is —(CH$_2$)$n^A$, wherein A is selected from the group consisting of carboxyl, carboxylic lower alkylester carboxylic amide group having the formula

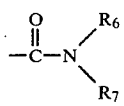

wherein $R_6$ and $R_7$ are the same or different and are selected from the group consisting of hydrogen and lower alkyl of from 1 to 8 carbon atoms, inclusive; cyano and an amine group having the formula

wherein $R''$ and $R'''$ are the same or different and are selected from the group consisting of hydrogen and alkyl of from 1 to 8 carbon atoms, inclusive; with the proviso that when $R_5$ is cyano or a carboxylic amide group, $R_3$ or $R_4$ must always be hydrogen; or a pharmaceutically acceptable salt of a compound wherein $R_5$ is an amine or a carboxyl group in combination with a pharmaceutically acceptable carrier.

9. A composition according to claim 8 wherein the compound has the formula

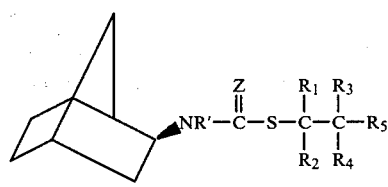

wherein $R_1$ thru $R_5$, $R'$, and $Z$ are the same as in claim 8.

10. A composition according to claim 9 wherein $R_5$ is carboxyl and $Z$ is sulfur.

11. A composition according to claim 10, Exo-($\pm$)-3-[[(bicyclo[2,2,1]hept-2-ylamino)thioxomethyl]thio]-propanoic acid.

12. A composition according to claim 8 having the formula

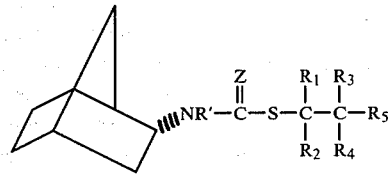

wherein $R_1$ thru $R_5$, $R'$, and $Z$ are the same as in claim 8.

13. A composition according to claim 12 wherein $R_5$ is carboxyl, and $Z$ is sulfur.

14. A composition according to claim 13, Endo-($\pm$)-3-[[(bicyclo[2,2,1]hept-2-ylamino)thioxomethyl]thio]-propanoic acid.

15. A method of producing immunosuppression in a mammal exhibiting a hyperimmunity disease which comprises systematically administering in a pharmaceutically acceptable dosage form a compound having the formula

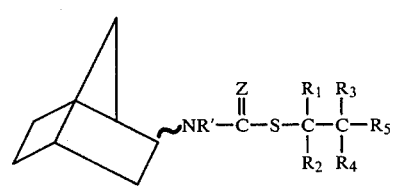

wherein $R_1$ thru $R_4$ are the same or different and are selected from the group consisting of hydrogen, alkyl of from 1 to 8 carbon atoms, inclusive; and aralkyl of from 7 to 20 carbon atoms, inclusive; R' is selected from the group consisting of hydrogen and alkyl of from 1 to 8 carbon atoms, inclusive; Z is selected from the group consisting of oxygen and sulfur; $R_5$ is $-(CH_2)n^4$, wherein Z is selected from the group consisting of carboxyl, carboxylic lower alkylester carboxylic amide group having the formula

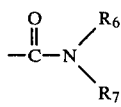

wherein $R_6$ and $R_7$ are the same or different and are selected from the group consisting of hydrogen and lower alkyl of from 1 to 8 carbon atoms, inclusive; cyano and an amine group having the formula

wherein R'' and R''' are the same or different and are selected from the group consisting of hydrogen and alkyl of from 1 to 8 carbon atoms, inclusive; with the proviso that when $R_5$ is cyano or a carboxylic amide group $R_3$ and $R_4$ must always be hydrogen; and pharmaceutically acceptable salts of compounds wherein $R_5$ is an amide or carboxyl group, in an amount effective to ameliorate or cure said hyperimmunity disease.

16. A method according to claim 15 wherein the compound is selected from the group consisting of Exo-($\pm$)-3-[[(bicyclo[2,2,1]hept-2-ylamino)thioxomethyl]-thio]propanoic acid, and endo-($\pm$)-3-[[(bicyclo[2,2,1]hept-2-ylamino)thioxomethyl]thio]propanoic acid.

17. A method of producing selective immunosuppression in a mammal exhibiting a hyperimmunity disease which comprises systematically administering in a pharmaceutically acceptable dosage form a compound having the formula

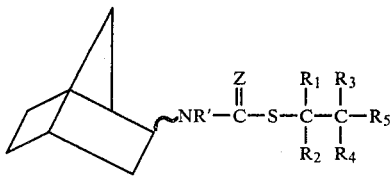

wherein $R_1$ thru $R_4$ are the same or different and are selected from the group consisting of hydrogen, alkyl of from 1 to 8 carbon atoms, inclusive; and aralkyl of from 7 to 20 carbon atoms, inclusive; R' is selected from the group consisting of hydrogen and alkyl of from 1 to 8 carbon atoms, inclusive; and Z is selected from the group consisting of oxygen and sulfur; $R_5$ is $-(CH_2)n^4$, wherein Z is selected from the group consisting of carboxyl, carboxylic alkylester, carboxylic amide group having the formula

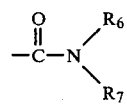

wherein $R_6$ and $R_7$ are the same or different and are selected from the group consisting of hydrogen and lower alkyl of from 1 to 8 carbon atoms, inclusive; cyano and an amine group having the formula

wherein R'' and R''' are the same or different and are selected from the group consisting of hydrogen and alkyl of from 1 to 8 carbon atoms, inclusive; with the proviso that when $R_5$ is cyano or a carboxylic amide group, $R_3$ or $R_4$ must always be hydrogen; and pharmaceutically acceptable salts of compounds wherein $R_5$ is an amine or carboxyl group.

18. A method according to claim 17 wherein the compound is selected from the group consisting of Exo-($\pm$)[[(bicyclo[2,2,1]hept-2-ylamino)thioxomethyl]thio]-propanoic acid and endo-($\pm$)-3-[[(bicyclo[2,2]hept-2-ylamino)thioxomethyl]thio]propanoic acid.

* * * * *